US008311302B2

(12) United States Patent
Yan et al.

(10) Patent No.: US 8,311,302 B2
(45) Date of Patent: Nov. 13, 2012

(54) METHOD FOR IDENTIFICATION OF DENTAL CARIES IN POLYCHROMATIC IMAGES

(75) Inventors: Jiayong Yan, Minhang (CN); Wei Wang, Minhang (CN); Liangliang Pan, Shanghai (CN); Victor C. Wong, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 176 days.

(21) Appl. No.: 12/965,945

(22) Filed: Dec. 13, 2010

(65) Prior Publication Data
US 2012/0148986 A1 Jun. 14, 2012

(51) Int. Cl.
G06K 9/00 (2006.01)
(52) U.S. Cl. ........................................ 382/128
(58) Field of Classification Search .................. 382/128
See application file for complete search history.

(56) References Cited

U.S. PATENT DOCUMENTS

| | | | |
|---|---|---|---|
| 4,479,499 A | 10/1984 | Alfano | |
| 5,570,182 A * | 10/1996 | Nathel et al. | 356/511 |
| 6,231,338 B1 * | 5/2001 | de Josselin de Jong et al. | 433/29 |
| 6,485,300 B1 * | 11/2002 | Muller et al. | 433/29 |
| 7,702,139 B2 | 4/2010 | Liang et al. | |
| 8,224,045 B2 * | 7/2012 | Burns et al. | 382/128 |
| 2004/0202356 A1 * | 10/2004 | Stookey et al. | 382/128 |
| 2008/0170764 A1 | 7/2008 | Burns et al. | |
| 2009/0185712 A1 | 7/2009 | Wong et al. | |

FOREIGN PATENT DOCUMENTS
EP 2083389 A2 7/2009

OTHER PUBLICATIONS

Commonly assigned U.S. Appl. No. 12/487,729, entitled "Method for Quantifying Caries", by Pan et al., filed Jun. 19, 2009.
European Search Report, Application No. EP 11 00 9777, dated Mar. 29, 2012, pp. 2.
Kevin Carter et al., Automated quantification of dental plaque accumulation using digital imaging, Journal of Dentistry, 2004, vol. 32, pp. 623-628.
Michael Thoms, Detection of intraoral lesions using a fluorescence camera, Proc. of SPIE, vol. 6137, pp. 7, 2006, XP040219947.

* cited by examiner

Primary Examiner — Tom Y Lu

(57) ABSTRACT

A method for identification of caries, executed at least in part on data processing hardware, obtains an original digital tooth image that has a plurality of color channels and generates an adjusted image by adjusting intensity values of the original digital tooth image to a range between a minimum value and a maximum value, wherein the adjusted image has at least a green channel image Iwgreen, a red channel image Iwred, and a blue channel image Iwblue. One or more tooth regions are segmented from gum and background regions within the adjusted image according to a relationship between two or more of the images Iwgreen, Iwred, and Iwblue to each other. One or more caries lesions is identified according to pixel intensity values from within the one or more segmented tooth regions, and the one or more tooth regions and the displayed and identified caries regions are highlighted.

31 Claims, 5 Drawing Sheets

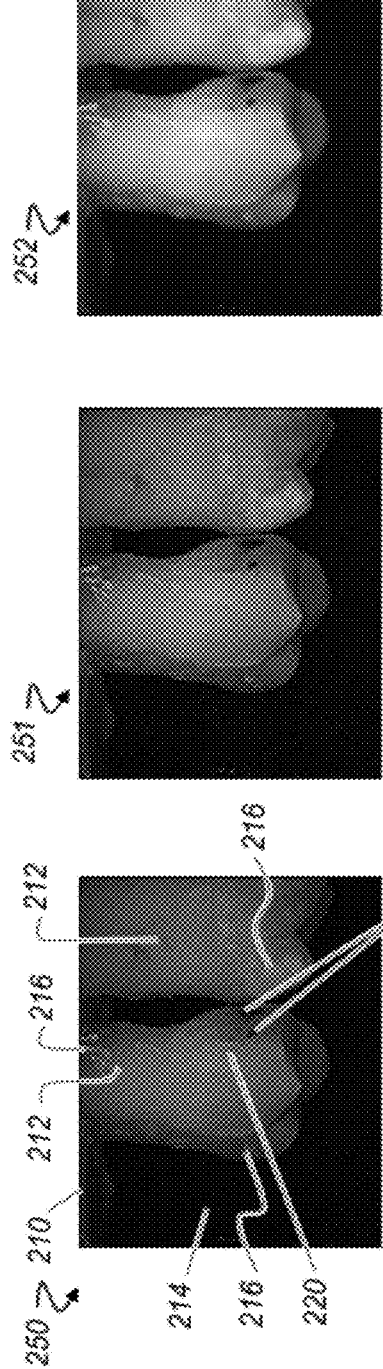

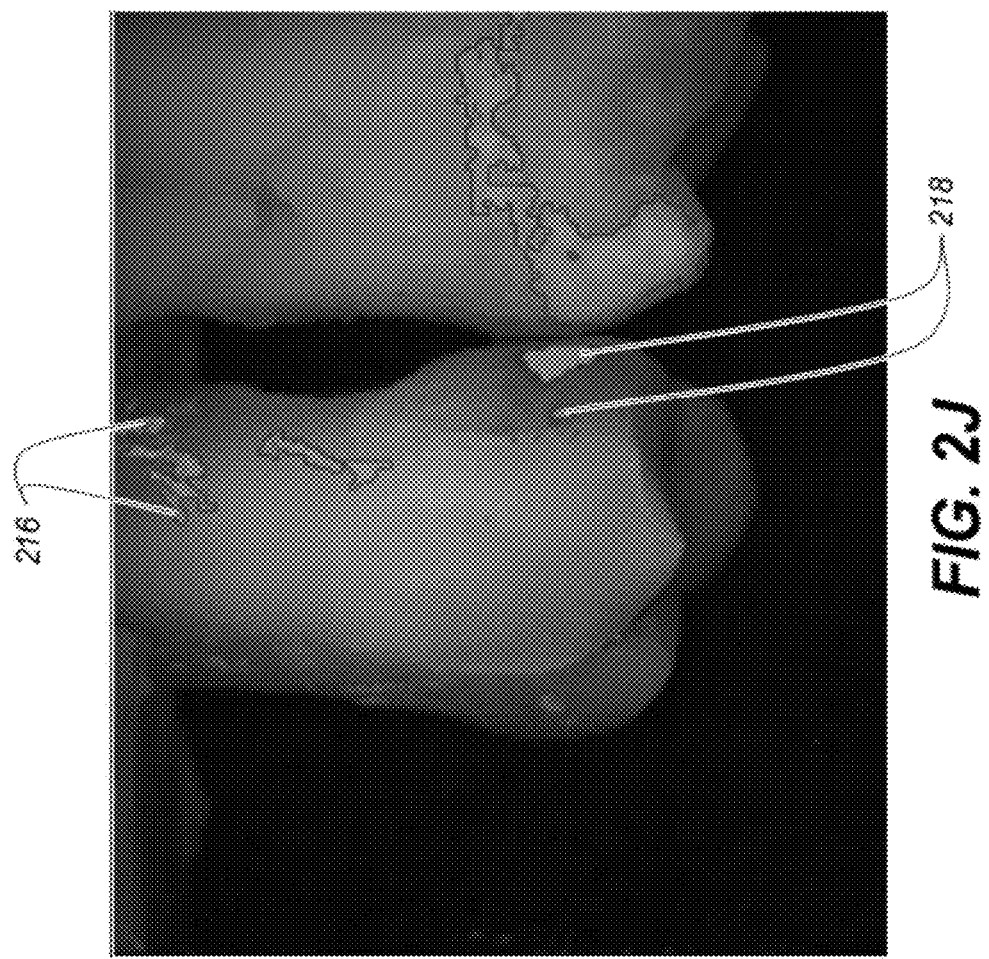

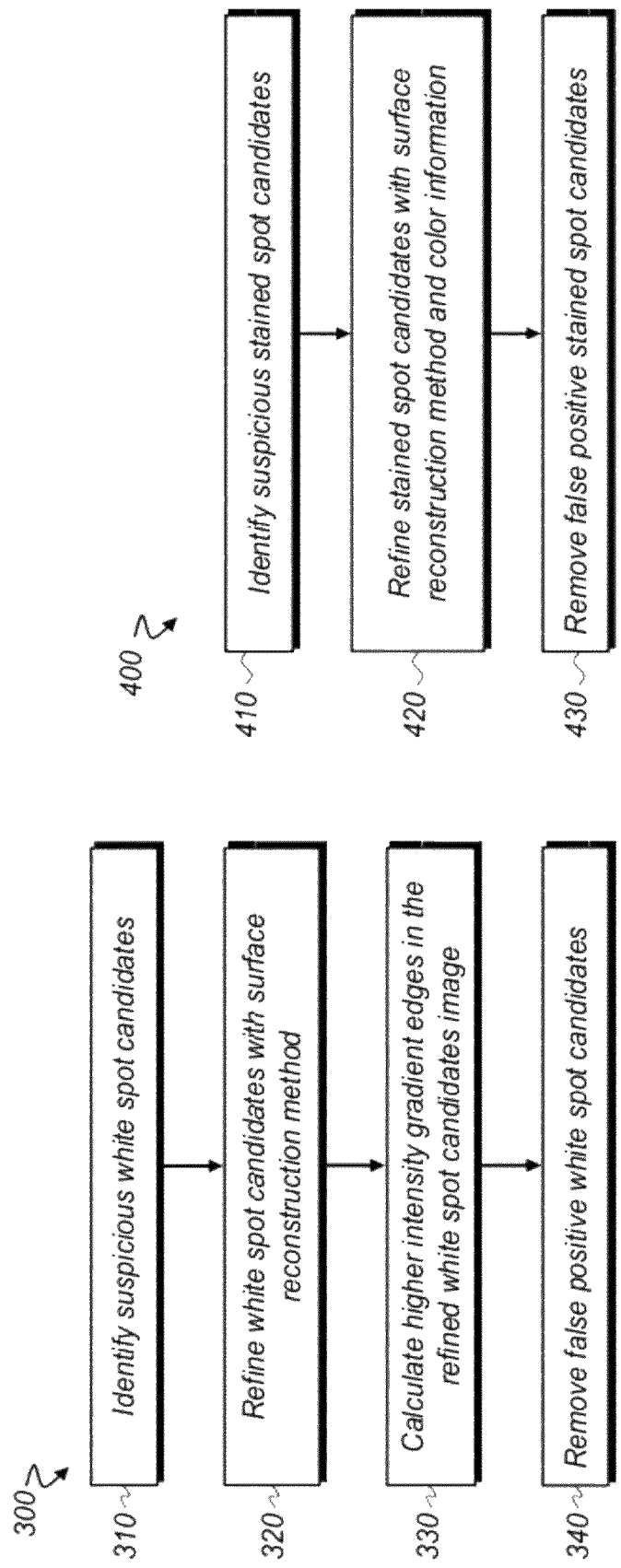

METHOD FOR IDENTIFICATION OF DENTAL CARIES IN POLYCHROMATIC IMAGES

FIELD OF THE INVENTION

The invention relates generally to the field of dental imaging, and in particular to a method and an apparatus for detection of caries. More specifically, the invention relates to a method and an apparatus for identifying and highlighting caries in displayed still and real-time video tooth images.

BACKGROUND OF THE INVENTION

While there have been improvements in detection, treatment and prevention techniques, dental caries remains a prevalent condition affecting people of all age groups. If not properly and promptly treated, caries could lead to permanent tooth damage and even to loss of teeth.

In response to the need for improved caries detection methods, various dental imaging systems, such as intraoral cameras, have been developed for early caries detection. One problem that existing dental imaging systems have in common is a long delay period between the time that the tooth is initially screened and the image of the tooth is obtained and the time that a possible caries condition is identified or reported to the dentist. With existing systems, tooth screening (during which the images are obtained) and caries detection (during which the images are processed and analyzed to identify carious regions) are carried out as two separate steps. In practice, at an appropriate point during screening, a still image capture is first obtained from the tooth in response to an operator instruction. Then, in a subsequent step, the image data are processed and analyzed for carious conditions to provide the clinician with a processed image (possibly also accompanied by a report) indicating caries information, such as apparent location, size, and severity, for example. This caries information is available only after the conclusion of the tooth screening step and only after image processing/analysis steps are completed. When the caries information becomes available at this later time after screening, the dentist often needs to go hack and re-examine the imaged tooth in order to look more closely at the reported problem area. This delay is inconvenient and lengthens the duration of the examination session. It can be appreciated that there would be an advantage to a method and an apparatus that would provide more immediate feedback to the examining practitioner, so that problem areas can be identified and examined more closely at the time of screening. However, this advantage is not available with conventional systems, due to factors such as the difficulty of detection, the intensive computation requirements needed for many existing detection methods, and the large amount of image data that is required for each tooth.

To solve the long delay problem, commonly assigned U.S. Patent Application Publication No. 2009/0185712 (Wong et al.) describes using region growing and global threshold methods to determine or segment tooth areas and caries areas, respectively. While this approach is workable under some conditions, performance can be hampered due to illumination variation, compromising the accuracy and robustness of results.

Thus there remains a need for an apparatus and a method that are capable of providing more immediate feedback to an examining practitioner so that caries areas can be identified and examined more closely at the time of screening, yet with reduced sensitivity to illumination variation.

SUMMARY OF THE INVENTION

An object of the present invention is to provide a method for real-time identification and highlighting of suspicious caries lesions in video images, particularly in live video intraoral camera images.

Another object of the present invention is to provide a method with reduced sensitivity to illumination variation for identification and highlighting of suspicious caries lesions.

Another object of the present invention is to provide a method for identification and highlighting of suspicious caries lesions by using a digital tooth image that is substantially free of specular reflection.

An advantage of the method according to the present invention is that it is more robust and accurate than the prior-art methods based on region growing and global threshold methods.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for identification of caries, executed at least in part on data processing hardware, the method comprising: obtaining an original digital tooth image that has a plurality of color channels; generating an adjusted image by adjusting intensity values of the original digital tooth image to a range between a minimum value and a maximum value, wherein the adjusted image comprises at least a green channel image Iwgreen, a red channel image Iwred, and a blue channel image Iwblue; segmenting one or more tooth regions from gum and background regions within the adjusted image according to a relationship between two or more of the images Iwgreen, Iwred, and Iwblue to each other; identifying one or more caries lesions according to pixel intensity values from within the one or more segmented tooth regions; and displaying the one or more tooth regions and highlighting the identified caries regions in the display.

According to another aspect of the invention, there is provided a method for identification of caries, executed at least in part on data processing hardware, the method comprising: obtaining an original digital tooth image that has a plurality of color channels; reducing specular reflection in the original digital tooth image to generate a conditioned original digital tooth image; generating an adjusted image by adjusting intensity values of the conditioned original digital tooth image to a range between a minimum value and a maximum value, wherein the adjusted image comprises at least a green channel image Iwgreen, a red channel image Iwred, and a blue channel image Iwblue; segmenting one or more tooth regions from gum and background regions within the adjusted image according to a relationship between two or more of the color channel images Iwgreen, Iwred, and Iwblue to each other; identifying one or more caries lesions according to pixel intensity values from within the one or more segmented tooth regions; and displaying the one or more tooth regions and highlighting the identified caries regions on the display.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 2A shows a typical digital tooth image.

FIG. 2B shows an adjusted image of the image shown in FIG. 2A.

FIG. 2C shows the green channel image of the adjusted image shown in FIG. 2

FIG. 2D shows tooth regions obtained by applying a threshold method to the green channel image shown in FIG. 2C.

FIG. 2E-1 shows suspicious white spot regions obtained by applying a local threshold method to the green channel image shown in FIG. 2C.

FIG. 2E-2 shows suspicious white spot regions refined with multi-resolution top-hat operations based on the image shown in FIG. 2E-1.

FIG. 2F-1 shows a reconstructed image obtained with a surface reconstruction methods.

FIG. 2F-2 shows the refined suspicious white spot regions based on the image shown in FIG. 2F-1.

FIG. 2G-1 shows a morphological gradient image of the green channel image shown in FIG. 2C.

FIG. 2G-2 shows the regions with high morphological gradients

FIG. 2J shows the detected white spots and stained spots overlapped on the original images.

FIG. 3 shows an embodiment of the step of identifying white spots.

FIG. 4 shows an embodiment of the step of identifying stained spots.

DETAILED DESCRIPTION OF THE INVENTION

Figure 1:
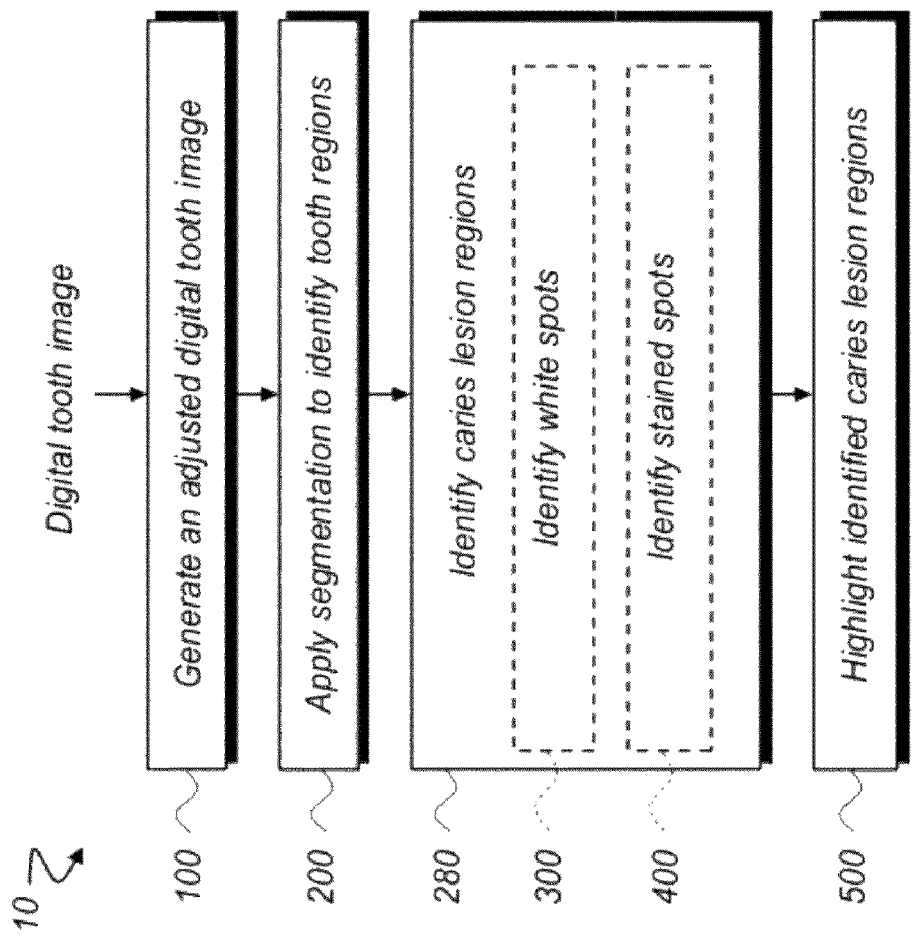
FIG. 1 shows a method for auto-highlighting caries in real-time video images comprising various steps according to the present invention.

The following is a detailed description of the preferred embodiments of the invention, reference being made to the drawings in which the same reference numerals identify the same elements of structure in each of the several figures.

Reference is made to commonly assigned U.S. Patent Application Publication No. 2009/0185712, by Wong et al entitled METHOD FOR REAL-TIME VISUALIZATION OF CARIES CONDITION filed on Jan. 22, 2008.

Reference is made to U.S. Ser. No. 12/487,729 entitled METHOD FOR QUANTIFYING CARIES by Pan et al., filed on Jun. 19, 2009, which published as PUBLICATION.

This invention includes calculation steps. Those skilled in the art will recognize that these calculation steps may be performed by data processing hardware that is provided with encoded instructions for image data processing. Because such image manipulation systems are well known, the present description is directed more particularly to algorithms and systems that execute the method of the present invention. Other aspects of such algorithms and systems, and data processing hardware and/or software for producing and otherwise processing the image signals may be selected from such systems, algorithms, components and elements known in the art. Given the description as set forth in the following specification, software implementation lies within the ordinary skill of those versed in the programming and image processing arts.

The stored instructions of such a software program may be stored in a computer readable storage medium, which may comprise, for example: magnetic storage media such as a magnetic disk or magnetic tape; optical storage media such as an optical disc, optical tape, or machine readable bar code; solid state electronic storage devices such as random access memory (RAM), or read only memory (ROM); or any other physical device or medium employed to store a computer program. Using such software, the present invention can be utilized on a data processing hardware apparatus, such as a computer system or personal computer, or on an embedded system that employs a dedicated data processing component, such as a digital signal processing chip.

In this disclosure, the word "auto-highlighting" refers to identifying and highlighting a lesion in a tooth image or image frame, generally accomplished by software without requiring user intervention.

In this disclosure, the word "intensity" is used to refer to light level, and is also broadly used to refer to the image value of a pixel in a digital image.

The term "white spots" is used to refer to the incipient caries lesions which have higher intensity than their surrounding normal/sound tooth regions in an image such as a reflectance image. It should be noted that white spots may indicate some other conditions with similar appearance in white light images, such as developmental hypomineralization, fluorosis, and arrested early caries, for example.

The term "stained spots" is used to include caries lesions that have been stained; generally more developed or advanced caries, which have lower intensity than their surrounding normal/sound tooth regions.

The term "white light" is used to refer to conventional broadband visible light illumination, such as that typically used for intra-oral cameras and image capture devices. The alternate term "polychromatic" refers to white light as well as to illumination from light sources of multiple wavelengths, such as from an illumination device that has separate sources, such as a red light source, a blue light source, and a green light source, for example.

The word "hole" in an image means a region, which is completely surrounded by higher intensity pixels. Specifically, in a binary image, the "hole" means a "0" region completely surrounded by "1" pixels.

The word "caries", unless otherwise noted, is used to refer to either early caries or developed/advanced caries.

The concept of "real-time" operation relates to the ability to display results of image processing during the time the intra-oral images are being obtained. In real-time operation, the dentist or technician can view detection results on a display while the teeth are being scanned by the camera. providing on-the-spot feedback to the practitioner.

For convenience, throughout this application, the terms starting with "I" referring to images, such as Iwred, Iwgreen and Iwblue, are also used to represent the intensity values of the pixels in the respective images.

According to an embodiment of the present invention shown in FIG. 1, a method 10 for real-time auto-highlighting caries comprises a step 100 of generating an adjusted image from an original digital tooth image, both the adjusted and original tooth images comprising actual intensity values for a region of pixels corresponding to the tooth, gum, and background; a segmentation step 200 for determining one or more tooth regions; a step 280 of identifying caries lesion regions; and a step 500 of highlighting segmented caries lesion regions in a displayed tooth image.

FIG. 1 shows that step 280 of identifying caries lesion regions comprises both step 300 of identifying or detecting one or more white spots and step 400 of identifying or detecting one or more stained spots according to one inventive example. In another example, step 280 of identifying caries lesion regions comprises step 300 but not step 400. In yet another example, step 280 comprises step 400 but not step 300. In still yet another example, step 280 includes neither step 300 nor step 400, but a step of detecting other type of caries.

Advantageously, all the steps 100, 200, 280, 300, 400, and 500 are performed automatically without a need for user input, and method 10's sensitivity to illumination variation is minimized.

Step 100 of Generating an Adjusted Digital Tooth Image

Herein, the term "digital tooth image" is used to represent a frame of a video tooth image or any static tooth image. Generally, a digital tooth image can be classified or segmented into three groups or regions: gum 210, tooth region 212, and other background 214. Caries identification and highlighting are only needed within tooth region 212.

According to one embodiment of the present invention, step 100 of generating an adjusted digital tooth image comprises sub-steps of obtaining an original digital tooth image and generating an adjusted image from the original digital tooth image.

FIG. 2A shows an original digital tooth image 250. In this particular example, original digital tooth image 250 is a white light reflectance image and has been conditioned to be substantially free of specular reflection. It is noteworthy that white light images captured from intraoral cameras typically contain specular reflections. Specular reflections have bright, whitish appearances that are very similar to incipient caries and confound early caries detection. For this reason, intraoral camera images generally cannot be used for early caries detection. In the present invention, specular reflections in the intraoral camera images have been removed to form the original tooth image 250, for example, by performing an additional image processing step, such as described in commonly assigned U.S. Patent Application Publication No. 2008/0170764, on the intraoral camera images. Alternatively, a original digital tooth image that is substantially free of specular reflection can be directly captured by a specially designed intraoral camera that compensates for this effect, such as the one disclosed in commonly assigned U.S. Pat. No. 7,702,139 using light of crossed polarizations. Advantageously, any white spot region in the specular reflection-free tooth image 250 can be unambiguously associated with incipient caries.

In the context of the present application, an image that is substantially free of specular reflection means that the contribution of specular reflection to the image intensity is less than 20%, more preferably less than 10%, and most preferably less than 5%.

Original digital tooth image 250 comprises one or more gum regions 210, one or more tooth regions 212, and background 214. Inside tooth regions 212 are one or more white spots 216, one or more stained spots 218, and one or more surrounding normal tooth regions 220. Original digital tooth image 250 can also be any other type of known image, captured with any known method. Typically, illumination level in the original tooth image undesirably varies with location. As is well known to those skilled in the optical design arts, it is difficult to design a low-cost optical system that can illuminate a complete field of view with equal light intensity.

FIGS. 2B-2J illustrate various intermediate and final images that are obtained during processing of the original digital tooth image.

FIG. 2B shows an adjusted image 251 of original digital tooth image 250 shown in FIG. 2A. Adjusted image 251 is formed by adjusting intensity values of original digital tooth image 250 to an intensity range that lies between a minimum value such as 0 and a maximum value such as 150. The purpose of forming adjusted image 251 is to reduce the impact of illumination variation on original digital tooth image 250. In one example, adjusted image 251 is linearly adjusted over the intensity range. Other methods of adjustment for compensating illumination variation can also be adopted.

Adjusted image 251 has a green channel image Iwgreen, a red channel image Iwred, and a blue channel image Iwblue. The letter "w" is used in Iwred, Iwgreen, and Iwblue because the adjusted image is formed from a "white" light reflectance image. A comparison of the red, green and blue channels generally shows that the green channel image of the adjusted image has a higher signal-noise-ratio than the red and blue channel images. Thus the green channel image is typically best suited for the steps of detecting white spots and stained spots. In general, some other channel image such as a red or blue channel image can also be used as long as it has a sufficiently high signal-noise-ratio. FIG. 2C shows the green channel image 252 of adjusted tooth image 251 shown in FIG. 2B.

Segmentation Step 200 for Tooth Regions 212

Segmentation step 200 for determining one or more tooth regions in adjusted digital tooth image 251 can be performed in a variety of ways. Normal/sound tooth areas are usually detected with a threshold method because they have higher intensity values than the background. According to one embodiment of the present invention, tooth regions 212 are determined according to the green channel image and a ratio image IWrgratio, where the ratio image IWrgratio is formed from the ratio of the red channel image Iwred over the green channel image Iwgreen, that is, IWrgratio=Iwred/Iwgreen. The details of determining tooth regions as part of this segmentation process are described below.

Firstly, a threshold image Iroi0 is generated from Iwgreen by selecting pixel intensity values higher than a predetermined threshold value T1. In one example. T1=20.

Secondly, a processed threshold image is generated by tilling the holes of the threshold image Iroi0, meaning that the regions having "0" value and surrounded by regions of "1" are replaced with "1".

Thirdly, gum regions are determined as part of this segmentation by using the ratio image IWrgratio=Iwred/Iwgreen. Because the gum is red, and the stained spots are typically brown. the ratio between red and green channels is found to be effective in detecting and distinguishing the gum from the stained spots. Two threshold images Igum0 and Igum1 are generated from the ratio image IWrgratio by selecting pixel intensity values higher than a relatively larger predetermined threshold value gumT0 and a relatively smaller predetermined threshold value gumT1, respectively. That is, gumT0>gumT1. For example, gumT0=1.8 and gumT1=1.4. The regions, which are in Igum1 and connected to objects in Igum0, are assigned as gum regions 210. This method has been proven to be accurate.

Lastly, tooth regions 212 are determined by removing gum regions 210 from the processed threshold image formed above. FIG. 2D shows an example of tooth regions 212 segmented from within original digital tooth image 250 illustrated in FIG. 2A and adjusted image 251 shown in FIG. 2B.

Compared to alternative methods such as region growing, step 200 has been shown to be more robust and accurate because of the use of the ratio image. The color information contained in the ratio image helps to discriminate gum from stained spots more effectively. Step 200 also has reduced sensitivity to illumination variation because the intensity of the adjusted image is normalized to within a certain range.

Step 300 of Identifying White Spots 216

In the green channel image Iwgreen of the adjusted white light tooth image, there is a definite morphological characteristic for one or more white spots, that is, the intensity values of white spots 216 are higher than those of the surrounding sound tooth regions 220. The present invention takes advantage of this characteristic to detect and segment the suspicious white spots mainly based on a morphological top-hat operation along with the multi-resolution, threshold methods, and surface reconstruction.

FIG. 3 shows one embodiment of step 300 of identifying white spots comprising sub-step 310 of identifying, or roughly determining, suspicious white spot candidates, sub-step 320 of refining white spot candidates with a surface reconstruction method, sub-step 330 of calculating high gradient edges in white spot candidates, and sub-step 340 of removing false positive white spot candidates from the refined white spot candidates by using the high gradient edges. The detailed sub-steps of identifying and segmenting the suspicious white spots are described as follows.

Sub-Step 310 of Identifying Suspicious White Spot Candidates

In one example, the suspicious white spot candidates are first roughly or coarsely identified by using a local threshold method. According to this method, a local threshold value Ithres(i, j) at pixel (i,j), formed at Row i and Column j, is first calculated for each pixel of the image Iwgreen using the following formula:

$$Ithres(i,j) = \min(I_{ave}(i), I_{ave}(j)) + T_{local};$$

where $I_{ave}(i)$ and $I_{ave}(j)$ are average intensity values of the pixels in the $i^{th}$ row and the $j^{th}$ column of the image Iwgreen over the tooth regions, respectively. $T_{local}$ is a predetermined constant parameter, for example 10, which is determined according to experiments and/or detection sensitivity and may vary depending on applications. Applying a threshold method using the local threshold value Ithres(i, j) at each pixel of the image Iwgreen results in a binary image Iwcan0. The binary image Iwcan0 represents very rough suspicious white spot regions shown in FIG. 2E-1, in which the pixel with value "1" belongs to the suspicious white spot candidates because the corresponding pixel value in Iwgreen is higher than the calculated local threshold value.

In order to refine or narrow the set of suspicious white spot candidates, according to the morphological characteristic of white spots 216, a morphological top-hat operation, along with multi-resolution and threshold methods, is applied to the green channel image Iwgreen.

The multi-resolution method is adopted because the size of the structure element used for morphological top-hat operation determines the size of the white spot that could be detected. Structure elements with different sizes can be used to detect white spots of different sizes. However, in order to fulfill the requirement for real-time operation, the original image Iwgreen is first down-sampled to form several reduced-resolution images, such as 2×-down sampled and 4×-down sampled images. Given a 2-dimensional shaped structure element with a fixed size, for example, a disk with a radius of 10 pixels, the morphological top-hat operation is then applied to the images with different resolutions (that is, 2×-down sampled image, 4×-down sampled image, etc.) to form respective multi-resolution top-hat images. Note that the 2-dimensional structure element can take other shapes. The size of the structure element, for example, the radius of the disk. can also be adjusted according to the image resolution or the size of the target objects.

After applying a threshold operation to each of the multi-resolution top-hat images, a binary image is obtained, inside of which the regions with a nonzero value are the white spot candidates in the image with corresponding resolution. The threshold value can be a fixed value, for example 7. It also can be empirically determined according to practical application. After interpolating each of the binary images back to the original resolution to produce interpolated images, the union of all the interpolated images is taken as image Iwcan1, in which the white spot candidates are represented with the "1", nonzero regions.

Figures 1, 2G:
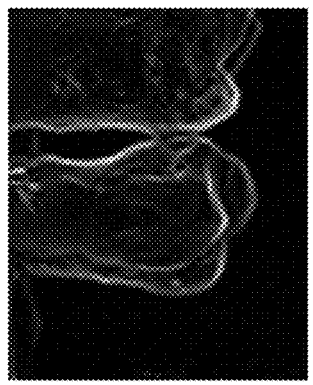
Figures 2, 2F:
Figures 1, 2F:
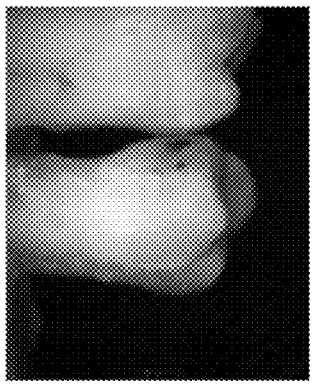
Figure 2I:
FIG. 2I shows a threshold image that is used to identify suspicious stained spots.

A white spot candidate image Iwcan2 shown in FIG. 2E-2 is then obtained according to Iwcan2=Iwcan0∩Iwcan1, in which the white spot candidates are represented with the "1", nonzero regions. The symbol ∩ is the intersection operator, familiar to those skilled in set theory.

Sub-Step 320 of Refining White Spot Candidates with a Surface Reconstruction Method Because only a limited number of resolutions can be used, and the size and shape of the structure elements are not the same as those of the white spots under detection, the white spot candidates identified in image Iwcan2 are usually not the optimal results. The present invention uses a method based on surface reconstruction to further refine the white spot candidate image Iwcan2 to generate a refined white spot candidate image Iwcan in two steps. First, a reconstructed image Ireconstructed shown in FIG. 2F-1 is formed by applying a surface reconstruction method to the white spot candidates represented by image Iwcan2. Here surface reconstruction means estimating the intensity values inside the white spot candidates as if they are normal tooth regions. The intensity estimation is a surface reconstruction processing. A variety of surface reconstruction methods such as linear interpolation, bilinear interpolation, two-dimensional spline fit, or Bezier fit, which have been discussed in commonly-assigned copending U.S. Ser. No. 12/487,729 entitled METHOD FOR QUANTIFYING CARIES by Pan et al., filed on Jun. 19, 2009, which published as PUBLICATION, can be used to estimate the intensities of pixels inside a certain region of an image.

Second, subtracting the reconstructed image Ireconstructed from the green channel image Iwgreen results in a difference image Idiff. Because the intensity values inside the white spots are higher than those of the normal/sound tooth regions, and the change between parts inside the normal or sound tooth areas is not as much as that between the white spots and the normal/sound tooth areas, the regions with intensity value change larger than a preset threshold value Tdiff (for example, >7, which can be adjusted according to the required detection sensitivity) are taken as the further refined white spot candidates image Iwcan shown in FIG. 2F-2, i.e., Iwcan=Idiff>Tdiff, in which the refined white spot candidates are represented with the "1", nonzero regions.

Sub-Step 330 of Calculating High Gradient Edges in White Spot Candidates

Because white spots contain little color information, it is difficult to remove false positive white spot candidates based on color information. According to the embodiment of the present invention, after the refined white spot candidate image Iwcan is obtained, the contrast feature of the tooth image Iwgreen is then used to reduce false positives from the white spot candidates. As a result, the white spot region is segmented from the normal tooth regions and background more accurately. One example of the contrast feature is the high gradient edges.

According to the embodiment of the present invention, the morphological gradient/grad, shown in FIG. 2G-1 of the image Iwgreen, is first calculated with Igrad=Iwgreen−imrode(Iwgreen,se), where the symbol intrude represents a gray scale image erode Operation, and "se" is a given structure element, for example a disk with a radius of 5, which is used for the erode operation. The image formed from the gray scale image erode operation shall be referred to as an eroded image. According to the required white spot detection sensitivity, given a gradient threshold Tgrad, the high gradient edges ledges, shown in FIG. 2G-2, can be obtained according to Iedges=Igrad>Tgrad.

Sub-Step 340 of Removing False Positive White Spot Candidates

It has been found that in a digital tooth image there may be more than one white spot. White spots often have significant local image features such as contrast. To reduce false positives by using contrast features, the refined white spot candidates in image Iwcan are investigated one by one and in a sub-window related to the digital image Iwgreen. For convenience, Iwinwgreen, Iwinwcan, Iwinedges, and Iwindiff are used to represent the corresponding sub-window images of Iwgreen, Iwcan, ledges and Idiff, respectively. For Iwinwcan and Iwinedges, all the pixels outside the white spot candidates under investigation are set to zero because only the pixels inside the target white spot candidate are investigated and considered.

Because one white spot candidate may have several edges, which may belong to one white spot or to different white spots, the edges of a white spot candidate are investigated one by one in the sub-window. For convenience, Iwinedge_i is used to represent the i-th connected edge in sub-window image Iwinedges.

According to one embodiment of the present invention, the white spots in Iwinwcan will be segmented and kept by investigating each edge Iwinedge_i and Iwinwcan, Iwindiff; and Iwinwgreen.

First, a potential false positive object, Iobj, is generated for a region in Iwinwcan, connected to Iwinedge_i and the respective values in Iwindiff higher than a threshold value Tdiff_i. Tdiff_i is calculated according to Tdiff_i=diffmean+w*diffstd, where diffmean is the mean and diffstd is the standard deviation of difference values between the pixels in Iwindiff and i-th connected edge in Iwinedge, and w is a weighting parameter, for example 0.0, which can be predetermined empirically according to the application.

Then, two rules are used to determine whether the potential false positive object Iobj is a white spot or a false positive. One rule is based on the percentage of the high gradient edges on the boundary of the potential false positive object Iobj. The other rule is based on the contrast between intensities of the pixels on the boundary of the potential false positive object Iobj and those of the surrounding normal/sound tooth. For white spots, either the edge percentage or the intensity contrast Should be higher than a certain threshold value. Otherwise, Iobj will be taken as a false positive.

Figure 2H:
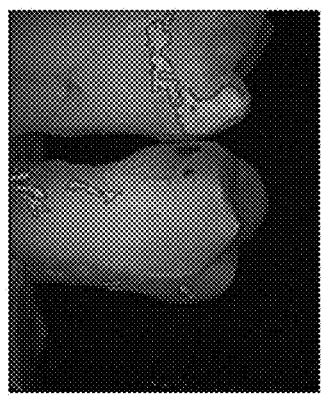
FIG. 2H shows the detected white spots after false positive white spot candidates are removed.
Figures 2, 2G:

FIG. 2H shows the identified white spots after false positive white spot candidates are removed.

Step 400 of Identifying Stained Spots 218

In a digital tooth image captured with a typical intra-oral camera, advanced caries lesion and stained tooth regions are very similar—both having lower intensity than their surrounding normal/sound tooth regions. Throughout this application, both advanced caries lesion and stained tooth regions are considered as stained spots.

According to one embodiment of the present invention, stained spots are identified with a global threshold method. In this method, first the green channel image Iwgreen of the digital tooth image is thresholded with a given global threshold value to form a threshold image shown in FIG. 2I. In one example, the global threshold value is 60. Note that this global threshold value depends on the detection sensitivity and the range of the adjusted image, which is between 0 and 150 in one embodiment as discussed earlier. Then the values of the pixels outside of tooth regions 212 determined above are set to zero because only the pixels inside the tooth regions are considered. Finally, the holes in the threshold image are taken as stained spot regions 218.

In the green channel image Iwgreen, there is a definite morphological characteristic for a stained spot, that is, the intensity values of stained spots 218 are lower than those of the surrounding sound tooth region 220. Another embodiment of the present invention takes advantage of this characteristic to detect and segment the suspicious stained spots mainly based on morphological bottom-hat operation along with multi-resolution threshold methods, and surface reconstruction. Because the suspicious stained spots and the surrounding normal tooth regions have different color information, the color information is also utilized for distinguishing spots according to the present invention. FIG. 4 shows that step 400 of identifying stained spots comprises sub-step 410 of identifying or roughly detecting suspicious stained spot candidates; sub-step 420 of refining stained spot candidates with a surface reconstruction method and color information to determine refined stained spot candidates; and sub-step 430 of removing false positive stained spot candidates from the refined stained spot candidates. The details of each sub-step are described below.

Sub-Step 410 of Identifying Suspicious Stained Spot Candidates

According to one embodiment of the present invention, the suspicious stained spot candidate image Iscan0, in which suspicious stained spot candidates are represented with the "1", nonzero regions, are first identified with a morphological bottom-hat operation along with the multi-resolution and threshold methods applied to the green channel of the digital tooth image Iwgreen. This sub-step is similar to the morphological top-hat operation along with the multi-resolution and threshold methods described in sub-step 310 except that the bottom-hat operation replaces the top-hat operation.

The multi-resolution method is adopted because the size of structure element used for morphological bottom-hat operation determines the size of the stained spot that could be detected. Structure elements with different sizes can be used to detect stained spots of different sizes. However, in order to fulfill real-time requirement, the original image Iwgreen is first down-sampled to form several reduced-resolution images, such as 2×-down sampled and 4×-down sampled images. Given a 2-dimensional shaped structure element with a fixed size, for example, a disk with a radius of 10 pixels, the morphological bottom-hat operation is then applied to the images with different resolutions (that is, 2×-down sampled image, 4×-down sampled image, etc.). Note that the 2-dimensional structure element can take other shapes. The size of the structure element, for example, the radius of the disk, can also be adjusted according to the image resolution or the size of the target objects.

Applying a threshold operation to each of the multi-resolution bottom-hat images, a binary image is obtained, inside which the regions with a nonzero value are the stained spot candidates in the image with corresponding resolution. The threshold value can be a fixed value, for example 7. It can also be determined according to practical application. After interpolating each of the binary images back to the original resolution, the union of all the interpolated images, or some other combination, is taken as suspicious stained spot candidate image Iscan0.

Sub-Step 420 of Refining Stained Spot Candidates with a Surface Reconstruction Method and Color Information Similar to sub-step 320, a surface reconstruction method is first used to generate a first reconstructed image Istained_rcon based on Iwgreen and Iscan0. With a predetermined threshold value Tstained_diff, the suspicious stained spot candidate image Iscan0 can be refined to form a first refined suspicious stained spot candidate image Iscan1, in which the first refined suspicious stained spot candidates are represented with the "1", nonzero regions, according to Iscan1=((Istained_recon−Iwgreen)>Tstained_diff)
∩Iscan0.

Tstained_diff can be adjusted according to the required detection sensitivity. In one example, Tstained_diff>7.

In a white light image captured by an intra-oral camera, the stained spots often appear as brown regions. According to this phenomenon, the color information is used to further refine the first refined suspicious stained spot candidate image IScan1. At first, according to the ratio image IWrgratio (IWrgratio=Iwred/Iwgreen) and image Iscan1, a second reconstructed image Irgratio_recon is generated. Then Iscan1 can be further refined to a second refined suspicious stained spot candidate image Iscan according to Iscan=(Idiffratio>Tdiffratio)∩Iscan1 where

Idiffratio=(Irgraio_recon−IWrgratio)/Irgratio_recon and Tdiffratio is a preset parameter that can be determined according to the practical application. In the second refined suspicious stained spot candidate image Iscan, second refined suspicious stained spot candidates are represented with "1" or nonzero regions. Alternately, the second refined suspicious stained spot candidates can be obtained with the edge information, alone or in combination with the color information.

Sub-Step 430 of Removing False Positive Stained Spot Candidates

Although they are refined with region interpolation and threshold methods, the second refined suspicious stained spot candidates may still include some false positives due to illumination variation, non-flat tooth surfaces, and noises, etc. Two main image features are used to detect and remove false positives: one is the intensity contrast, and the other one is holes in gray scale image. Generally, the intensity values of stained spots in Iwgreen image are lower than that of the surrounding normal tooth regions, and the ratios of stained spots in ratio image IWrgratio are higher than those of the surrounding normal tooth regions. According to the intensity and color ratio contrast, the second refined suspicious stained spot candidates in image Iscan are first investigated in a one-by-one manner using a method similar to that used for investigating Iwcan. For stained spots, either the intensity contrast or the color ratio contrast should be higher than an empirically determined threshold value. Otherwise, the candidate under investigation will be taken as a false positive.

Next, the stained spot candidates located near interproximal regions are investigated. Because it is not easy to detect and locate the interproximal regions, the present invention mainly uses the contour curvature of tooth regions 212 and bottom-hat of Iwgreen to estimate the positions of the interproximal regions. For each point on the boundaries of tooth regions 212, if the curvature is high and concave, it will be taken as a point locating at the interproximal regions, referred to as an interproximal point. The range of the curvature is determined according to practical application. It is seen from image Iwgreen that the interproximal regions also usually have lower intensity values than their surrounding normal tooth areas. Therefore, a bottom-hat operation will be applied to Iwgreen to generate a bottom hat image. If a region, whose value in the bottom hat image is lower than a preset threshold value; is connected with any detected interproximal point detected, it will be taken as an interproximal region. For removal of false positives caused by interproximal regions, the updated stained spot candidates given by Iscan_updated and connected to the detected interproximal regions are analyzed, and only the corresponding "holes" in Iwgreen are retained as stained spot candidates.

Step 500 of Highlighting the Determined Caries Lesion Regions

This step is essentially the same as the step of "caries highlighting" shown in FIG. 3 of commonly assigned U.S. Patent Application Publication No. 2009/0185712 (Wong et al.). The pixels corresponding to the identified caries lesions, such as white and stained spots, are modified or highlighted in some way in order to create an exaggerated visual effect that attracts viewer attention in a viewable image frame or still image as shown in FIG. 2J. Accordingly, white spots and stained spots are highlighted differently to elucidate the different conditions of the suspicious lesions. Furthermore, different highlighting can be used to indicate different white spot conditions, such as active incipient lesions, developmental hypomineralization, fluorosis, and arrested early caries, for example.

Pixel modification can be carried out in a number of ways. In one embodiment, pixel values in one color plane are mapped to higher intensity values. In other embodiments, more complex image processing is performed, using techniques such as adding false-color effects, such as highlighting using synthetic colors or displaying other colors not expected to be sensed within the mouth. Outlining or shading can alternately be used. Alternative forms of pixel modification could also be utilized for more clearly highlighting the detected caries sites.

Although the method according to the present invention is based only on polychromatic images such as white light images, it can be easily adjusted and expanded to other intra-oral camera images like fluorescence-based images. This method can be applied using image data that is stored in separate color planes, such as in a red, green, or blue color plane, as well as using image data in which the color information is interleaved or otherwise represented.

It is emphasized that the method according to the present invention. when implemented on state-of-the-art data processing hardware, can operate in very high speed. Accordingly, it is suitable for real-time operation with video images of teeth, for which image content within each color channel is obtained a number of time per second. But it is equally applicable to still images of teeth, obtained in a single image capture operation. This method can also be used for analyzing and displaying caries information from stored digital images.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A method for identification of caries, executed at least in part on data processing hardware, comprising:
   obtaining an original digital tooth image that has a plurality of color channels;
   generating an adjusted image by adjusting intensity values of the original digital tooth image to a range between a minimum value and a maximum value, wherein the adjusted image comprises at least a green channel image Iwgreen, a red channel image Iwred, and a blue channel image Iwblue;
   segmenting one or more tooth regions from gum and background regions within the adjusted image according to a relationship between two or more of the images Iwgreen, Iwred, and Iwblue to each other;
   identifying one or more caries lesions according to pixel intensity values from within the one or more segmented tooth regions; and
   displaying the one or more tooth regions and highlighting the identified caries regions in the display.

2. The method of claim 1, wherein identifying the one or more caries lesion regions comprises detecting one or more white spots or detecting one or more stained spots.

3. The method of claim 2, wherein detecting the one or more white spots comprises:
   identifying one or more suspicious white spot candidates from within the one or more segmented tooth regions;
   refining the one or more identified white spot candidates to form one or more refined white spot candidates;
   calculating one or more gradient edges in the one or more refined white spot candidates; and
   removing one or more false positive white spot candidates from the one or more refined white spot candidates according to the calculated gradient edges or intensity contrast.

4. The method of claim 2, wherein detecting the one or more stained spots comprises:
   identifying one or more suspicious stained spot candidates from within the one or more segmented tooth regions;
   refining the one or more stained spot candidates to form one or more refined stained spot candidates; and
   removing one or more false positive stained spot candidates from the one or more refined stained spot candidates.

5. The method of claim 3, wherein identifying the one or more suspicious white spot candidates comprises applying a local threshold method.

6. The method of claim 3, wherein identifying the one or more suspicious white spot candidates comprises applying a morphological top-hat operation to the one or more segmented tooth regions at a plurality of resolutions and applying a local threshold method.

7. The method of claim 3, wherein refining the one or more identified white spot candidates comprises applying a surface reconstruction method.

8. The method of claim 3, wherein calculating the one or more gradient edges in the one or more refined white spot candidates comprises applying a gray scale image erode operation on one or more of the red, green, or blue channel images.

9. The method of claim 4, wherein identifying one or more suspicious stained spot candidates comprises applying a morphological bottom-hat operation to the one or more segmented tooth regions at a plurality of resolutions and applying a local threshold method.

10. The method of claim 4, wherein refining the one or more stained spot candidates comprises applying a surface reconstruction method.

11. The method of claim 4, wherein removing the one or more false positive stained spot candidates comprises using intensity contrast or the ratio between two or more color channel images.

12. The method of claim 4, wherein removing the one or more false positive stained spot candidates comprises using contour curvatures to locate one or more interproximal regions and to retain one or more holes formed in the image data for the one or more segmented tooth regions.

13. The method of claim 2 further comprising highlighting caries regions differently according to information about the detected caries condition.

14. The method of claim 1, wherein the original digital tooth image is obtained from a white light image.

15. The method of claim 1, further comprising conditioning the content of the original digital tooth image to reduce specular reflection.

16. The method of claim 15 wherein conditioning the content of the original digital tooth image comprises processing the original image data.

17. The method of claim 1, wherein the original digital tooth image is a video image.

18. The method of claim 1, wherein displaying the one or more tooth regions comprises displaying the regions as images are being obtained from the patient.

19. The method of claim 1 wherein segmenting the one or more tooth regions comprises:
   selecting a channel image from the red, green, and blue channel images, the selected channel image having a higher signal-to-noise ratio than the other two channel images;
   identifying one or more tooth regions according to a ratio image formed by the ratio of the red channel image Iwred to the selected channel image; and
   revising the tooth region identification, comprising:
      (a) applying a threshold method to the selected channel image by selecting pixel intensity values higher than a predetermined threshold value to generate a threshold image;
      (b) filling one or more holes of the threshold image to form a processed threshold image; and
      (c) identifying the tooth region by identifying and removing one or more gum regions from the processed threshold image.

20. The method of claim 1, wherein generating an adjusted image comprises adjusting the intensity values of the original digital tooth image to be linear between the minimum and maximum values.

21. The method of claim 1, wherein the relationship between two or more of the Iwgreen, Iwred, and Iwblue images is a ratio of the red channel image Iwred over the green channel image Iwgreen.

22. The method of claim 1, wherein the original digital tooth image is a still image.

23. The method of claim 15 wherein conditioning the content of the original digital tooth image to reduce specular reflection comprises using cross-polarized light on an image capture apparatus.

24. A method for identification of caries, executed at least in part on data processing hardware, the method comprising:
   obtaining an original digital tooth image that has a plurality of color channels;

reducing specular reflection in the original digital tooth image to generate a conditioned original digital tooth image;

generating an adjusted image by adjusting intensity values of the conditioned original digital tooth image to a range between a minimum value and a maximum value, wherein the adjusted image comprises at least a green channel image Iwgreen, a red channel image Iwred, and a blue channel image Iwblue;

segmenting one or more tooth regions from gum and background regions within the adjusted image according to a relationship between two or more of the color channel images Iwgreen, Iwred, and Iwblue to each other;

identifying one or more caries lesions according to pixel intensity values from within the one or more segmented tooth regions; and displaying the one or more tooth regions and highlighting the identified caries regions on the display.

25. The method of claim 24 wherein reducing specular reflection comprises using cross-polarized light on an image capture apparatus.

26. The method of claim 24 wherein reducing specular reflection comprises processing the tooth image data.

27. A method for tooth region segmentation, executed at least in part on data processing hardware, the method comprising:

obtaining an original digital tooth image that has a plurality of color channels;

generating an adjusted image by adjusting intensity values of the original digital tooth image to a range between a minimum value and a maximum value, wherein the adjusted image comprises at least a green channel image Iwgreen, a red channel image Iwred, and a blue channel image Iwblue;

selecting a channel image from the red, green, and blue channel images, the selected channel image having a higher signal-to-noise ratio than the other two channel images;

identifying one or more tooth regions according to a ratio image formed by the ratio of the red channel image Iwred to the selected channel image; and revising the tooth region identification, comprising:
(i) applying a threshold method to the selected channel image by selecting pixel intensity values higher than a predetermined threshold value to generate a threshold image;
(ii) filling one or more holes of the threshold image to form a processed threshold image; and
(iii) identifying the tooth region by identifying and removing one or more gum regions from the processed threshold image.

28. The method of claim 27 wherein identifying the one or more gum regions comprises applying a threshold method to the ratio image by selecting pixel intensity values higher than predetermined first and second threshold values gumT0 and gumT1, respectively, to generate corresponding threshold images Igum0 and Igum1, respectively, the regions in Igum1 and connected to objects in Igum0 being assigned as gum regions, wherein gumT0>gumT1.

29. The method of claim 27, wherein the intensity values of the adjusted image are linearly adjusted between the minimum and maximum values.

30. The method of claim 27, wherein the selected channel image is the green channel image.

31. The method of claim 27, wherein the original digital tooth image is obtained using white light.

* * * * *